United States Patent [19]
Zhang et al.

[11] Patent Number: 6,083,532
[45] Date of Patent: Jul. 4, 2000

[54] SUSTAINED RELEASE FORMULATION CONTAINING THREE DIFFERENT TYPES OF POLYMERS AND TABLET FORMED THEREFROM

[75] Inventors: Guohua Zhang, Parsippany; Prasad Pinnamaraju; Muhammad Ali, both of Edison, all of N.J.

[73] Assignee: Duramed Pharmaceuticals, Inc., Cincinnati, Ohio

[21] Appl. No.: 08/985,986

[22] Filed: Dec. 5, 1997

Related U.S. Application Data

[63] Continuation-in-part of application No. 08/395,565, Mar. 1, 1995, Pat. No. 5,695,781.

[51] Int. Cl.⁷ ................................................. A61K 9/22
[52] U.S. Cl. ....................... 424/468; 424/469; 424/470; 514/772.3; 514/779; 514/781; 514/782; 514/960; 514/961; 514/964; 514/965
[58] Field of Search ................................. 424/465, 468, 424/469, 470

[56] References Cited

U.S. PATENT DOCUMENTS

| | | | |
|---|---|---|---|
| 3,261,859 | 7/1966 | Dengel | 260/465 |
| 4,157,394 | 6/1979 | Fleckenstein et al. | 424/251 |
| 4,461,759 | 7/1984 | Dunn | 424/19 |
| 4,654,372 | 3/1987 | Marcoux | 514/646 |
| 4,697,035 | 9/1987 | Kisielowski et al. | 558/344 |
| 4,708,874 | 11/1987 | De Haan et al. | 424/470 |
| 4,753,803 | 6/1988 | Stephens et al. | 424/467 |
| 4,792,452 | 12/1988 | Howard et al. | 424/475 |
| 4,798,811 | 1/1989 | Lehmann et al. | 514/159 |
| 4,800,081 | 1/1989 | Albrecht et al. | 424/129 |
| 4,832,958 | 5/1989 | Baudier et al. | 424/473 |
| 4,859,469 | 8/1989 | Baudier et al. | 424/462 |
| 4,863,742 | 9/1989 | Panoz et al. | 424/473 |
| 4,952,672 | 5/1990 | Gremm et al. | 424/451 |
| 4,981,871 | 1/1991 | Abelson | 514/523 |
| 5,047,235 | 9/1991 | Lossnitzer et al. | 424/80 |
| 5,089,502 | 2/1992 | Sudilovsky et al. | 514/274 |
| 5,128,142 | 7/1992 | Mulligan et al. | 424/457 |
| 5,132,119 | 7/1992 | Lee | 424/646 |
| 5,132,295 | 7/1992 | Balz et al. | 514/54 |
| 5,169,639 | 12/1992 | Baichwal et al. | 424/468 |
| 5,230,901 | 7/1993 | Einig et al. | 424/468 |
| 5,252,337 | 10/1993 | Powell | 424/456 |
| 5,350,771 | 9/1994 | Pang et al. | 514/643 |

FOREIGN PATENT DOCUMENTS 1184497  3/1985  Canada .

OTHER PUBLICATIONS

Excerpts from the *Handbook of Pharmaceutical Excipients*, Second Edition, published by the American Pharmaceutical Association.

*Primary Examiner*—James M. Spear
*Attorney, Agent, or Firm*—Shook, Hardy & Bacon L.L.P.

[57] ABSTRACT

Depot drug formulations include the pharmaceutical itself and a three component release rate controlling matrix composition. The three components of the matrix composition are (1) a pH dependent gelling polymer such as an alginate component, (2) an enteric polymer component, such as Eudragit® L or S, and (3) a pH independent gelling polymer, such as hydroxy propyl methyl cellulose or polyethylene oxide. The drug release rate can be adjusted by changing the amount of one or more of these components of the composition.

47 Claims, No Drawings

SUSTAINED RELEASE FORMULATION CONTAINING THREE DIFFERENT TYPES OF POLYMERS AND TABLET FORMED THEREFROM

CROSS REFERENCE TO RELATED APPLICATION

This application is a continuation-in-part of prior copending application Ser. No. 08/395,565, filed Mar. 1, 1995 U.S. Pat. No. 5,695,781, the entirety of the disclosure of which is hereby specifically incorporated herein by reference.

FIELD OF THE INVENTION

The present invention is directed to formulations for preparing sustained release drug forms useful for releasing pharmaceuticals at controlled rates, generally in the stomachs and/or gastrointestinal tracts of hosts. In particular the invention relates to an improved depot drug form useful in connection with preparing sustained release tablets.

BACKGROUND OF THE INVENTION

A zero order release profile for a drug from its controlled release dosage form sometimes is desirable in clinical use. The technology used to formulate zero order release dosage forms is well documented. The entrapment of a drug in a matrix is a common approach to formulate sustained release tablets with a zero order release profile.

It has been reported that depot drug formulations for controlled release of pharmaceutical drugs may be prepared using alginates alone (see U.S. Pat. No. 5,132,295), using combinations of alginates and polyacrylates (see U.S. Pat. No. 5,230,901) and using combinations of alginates and a pH independent hydrocarbon gelling agent, such as, for example, hydroxypropylmethyl cellulose (see U.S. Pat. No. 4,792,452). It is also known that the use of alginates alone for this purpose often presents difficulties in tableting, film coating and storage.

Adding polyacrylates to the alginate formulation overcomes these difficulties to some extent; however, tablets formed using alginates and polyacrylates often have a pH dependent dissolution profile. In a low pH environment, alginates and polyacrylates do not swell and/or dissolve properly. This leads to drug release by a diffusion mechanism through non-viscous capillaries resulting in a different dissolution rate than in a high pH environment. On the other hand, in a high pH environment, alginates swell and become soluble while polyacrylates may or may not do the same. This leads to drug release both by erosion and diffusion at a rate which is different than the low pH release rate.

In formulations which include an alginate and a pH independent gelling polymer such as, for example, hydroxypropylmethyl cellulose, such polymers hydrate at low pH levels to create a viscous gel layer for drug release. At high pH levels, however, tablets become smaller and smaller during drug release due to polymer erosion, and this leads to a reduction in surface area which may affect dissolution rate.

SUMMARY OF THE INVENTION

A novelty of the present invention is the provision of a sustained release formulation which reduces, and perhaps eliminates these problems completely. In particular the invention provides a controlled release drug formulation which includes 1) a pH dependent gelling polymer such as, for example, an alginate material, a carboxyvinyl polymer or a sodium salt of carboxymethyl cellulose, 2) an enteric polymer, such as, for example, a cellulose acetate phthalate, a cellulose phthalate hydroxy propyl methyl ether, a polyvinyl acetate phthalate, a hydroxy propyl methyl cellulose acetate succinate, a cellulose acetate trimellitate, a shellac or a polyacrylate material such as Eudragit® L or Eudragit® S, and 3) a pH independent gelling polymer, such as, for example, a hydroxy propyl methyl cellulose, a hydroxy propyl ethyl cellulose, a hydroxy propyl cellulose, a hydroxy ethyl cellulose, a methyl cellulose, a xantham gum or a polyethylene oxide. Such a combination of ingredients facilitates manufacturing procedures and improves drug dissolution profile.

In the formulation in accordance with the present invention, the pH dependent gelling polymer provides excellent binding and controlled release characteristics thereby facilitating the manufacturing processes. During dissolution, the pH independent gelling polymer hydrates to form a gel layer to control drug release at low pH levels. At high pH levels, the enteric polymer increases erosion rate so as to maintain a constant dissolution rate regardless of tablet size. So reduction in tablet size does not reduce release rate. Thus, the formulations of the present invention provide improved drug release profiles compared with the prior art formulations described above.

DETAILED DESCRIPTION OF THE PREFERRED EMBODIMENTS

The present invention provides sustained release tablets formulated with a mixture of a pharmaceutical composition, a pH dependent gelling polymer, an enteric polymer and a pH independent gelling polymer from which the pharmaceutical composition may be released at a controlled rate. In a particularly preferred form of the invention, the formulation may be used to provide a depot drug form for controlled release of a verapamil containing pharmaceutical composition. However, the formulation is also useful in connection with a variety of other pharmaceutical or active compositions, including water soluble compositions, water sparingly soluble compositions and water insoluble compositions, and therefore the invention should not be considered as being limited by the exact composition and/or nature of the pharmaceutical or other active composition which is released under controlled conditions therefrom.

In a preferred form, the formulation of the invention may contain 1) a pH dependent gelling polymer such as an alginate component in the form of a water soluble salt of an alginic acid having a viscosity within the range of from about 60 to about 10,000 centipoises, and preferably from about 100 to about 6,000 centipoises, in a 2% by weight water solution at 25° C., as measured by a Brookfield LV viscometer; 2) an enteric polymer composition component, such as a cellulose derivative or a methacrylic acid copolymer (preferably Eudragit® L/S); and 3) a pH independent gelling polymer component, such as a cellulose derivative or polyethylene oxide, having a viscosity within the range of from about 10 to about 100,000 centipoises, and preferably from about 50 to about 15,000 centipoises in a 2% by weight water solution at 20° C.

The active drug content in the overall tablet formulation may preferably range from about 0.5% to about 70% by weight. The total amount of the gelling and enteric polymers in the overall tablet formulation may preferably range from about 8% to about 65% by weight. The total amount of the pH dependent gelling polymer in the overall tablet formulation may preferably range from about 2% to about 60% by weight. The total amount of the pH independent polymer in the overall tablet formulation may preferably range from about 2% to about 55% by weight. The total amount of the enteric polymer in the overall tablet formulation may preferably range from about 1% to about 55% by weight.

Suitable enteric polyacrylate materials are described, for example, in U.S. letters Pat. No. 5,230,901, the entirety of the disclosure of which is incorporated herein by reference. In this regard, the term polyacrylate is used herein to encompass the polyacrylates, the polymethacrylates and the copolymers of acrylic and methacrylic acid disclosed in the '901 patent. These materials are also described in, for example, Houben-Weyl, Methoden der organischen Chemie, Thieme-Verlag, Stutt, 1961. Products which are commercially available under the name Eudragit®, for example Eudragit® L and Eudragit® S, are particularly suitable. Other suitable enteric polymers include, for example, cellulose derivatives such as cellulose acetate phthalate, cellulose phthalate hydroxy propyl methyl ether, hydroxy propyl methyl cellulose acetate succinate, cellulose acetate trimellitate, and substances such as polyvinyl acetate phthalate, shellac and polymethacrylates, etc.

Other ingredients which may be optionally included in the formulation of the invention include 1) one or more binders such as, for example, povidone (polyvinylpyrrolidone), modified starch, low viscosity hydroxypropylmethyl cellulose, etc.; 2) one or more fillers such as, for example, microcrystalline cellulose, lactose, starch, calcium sulfate, etc.; 3) one or more lubricants such as, for example, magnesium stearate, stearic acid, etc.; 4) one or more coating film formers such as, for example, Opadry (a hydroxypropylmethyl cellulose based coating system); and 5) one or more colorants such as, for example, FD&C green dye. The binder materials may be present in an amount up to about 100 by weight of the entire formulation and the lubricant materials may be present in an amount within the range of from about 0.10% to about 5.0% by weight of the entire formulation.

In the specific examples set forth below, three specific embodiments of the invention for releasing verapamil HCl are exemplified. These embodiments have been designated A, B and C.

SPECIFIC EXAMPLES OF PREFERRED EMBODIMENTS

| COMPONENT | AMOUNT OF COMPONENT IN EACH EMBODIMENT | | |
|---|---|---|---|
| | A | B | C |
| 1. VERAPAMIL HCL | 240 MG | 120 MG | 240 MG |
| 2. SODIUM ALGINATE | 250 MG | 80 MG | 200 MG |
| 3. HYDROXYPROPYLMETHYL CELLULOSE | 50 MG | 15 MG | — |
| 4. POLYETHYLENE OXIDE | — | — | 60 MG |
| 5. METHACRYLIC ACID COPOLYMER (® Eudragit L/S) | 120 MG | 30 MG | 100 MG |
| 6. POVIDONE | 50 MG | 25 MG | 40 MG |
| 7. MICROCRYSTALLINE CELLULOSE | 60 MG | 80 MG | 80 MG |
| 8. MAGNESIUM STEARATE | 5 MG | 2 MG | 5 MG |

Items 1 through 7 listed above are mixed in a mixer such as a high shear mixer granulator or planetary mixer to obtain homogeneity. The mix is then granulated in water or other suitable granulation fluids and dried in a dryer. The dried granular mass is then milled and then item 8 (a lubricant) is added during milling. The lubricated granular mass is then compressed into tablets using a tablet press. The foregoing steps are conventional steps used in the tablet forming industry.

In the preferred embodiments set forth above, the formulations of the invention have particular utility in the preparation of sustained release tablets of verapamil. However, the invention is not limited to use in connection with this drug only. Tablets containing other drugs requiring sustained release are as well within the intended scope of the invention. It is contemplated that the sustained release formulations of the invention have utility in connection with drugs which are water soluble, water sparingly soluble or water insoluble. For example, suitable pharmaceutical drugs which may require sustained release and which therefore are within the scope of the present invention are listed in U.S. Pat. No. 4,792,452 to Howard et al., the entirety of the disclosure of which is hereby specifically incorporated by reference.

Specific examples of formulations of the invention which may be used with drugs other than verapamil are as follows:

| COMPONENT | AMOUNT OF COMPONENT IN EACH EMBODIMENT | |
|---|---|---|
| | A | B |
| 1. PENTOXYFILLINE | 400 MG | 600 MG |
| 2. SODIUM ALGINATE | 60 MG | 80 MG |
| 3. HYDROXYPROPYLETHYL CELLULOSE | 50 MG | 120 MG |
| 4. EUDRAGIT ® | 20 MG | 20 MG |
| 5. POVIDONE | 25 MG | 40 MG |
| 6. MICROCRYSTALLINE CELLULOSE | 42 MG | 55 MG |
| 7. MAGNESIUM STEARATE | 3 MG | 5 MG |
| 1. NIFEDIPINE | 90 MG | 60 MG |
| 2. SODIUM CARBOXY METHYL CELLULOSE | 30 MG | 12 MG |
| 3. HYDROXY PROPYL METHYL CELLULOSE | 30 MG | 36 MG |
| 4. CELLULOSE ACETATE PHTHALATE | 10 MG | 12 MG |
| 5. POVIDONE | 16 MG | 14 MG |
| 6. LACTOSE | 112 MG | 74 MG |
| 7. MICROCRYSTALLINE CELLULOSE | 30 MG | 30 MG |
| 8. MAGNESIUM STEARATE | 2 MG | 2 MG |

Tablets based on the formulations described above incorporating pentoxyfilline and nifedipine may be prepared using procedures which are essentially the same as the procedure described previously for preparing tablets based on formulations incorporating verapamil.

We claim:

1. A tablet for sustained release of a drug comprising an effective amount of a drug to be released at a controlled rate and a sustained release formulation, said sustained release formulation comprising at least three different types of polymers including a pH dependent gelling polymer, a pH independent gelling polymer and an enteric polymer, wherein said pH dependent gelling polymer comprises at least one of an alginate, a carboxyvinyl polymer, or a salt of a carboxymethyl cellulose.

2. A tablet for sustained release of a drug comprising an effective amount of a drug to be released at a controlled rate and a sustained release formulation, said sustained release formulation comprising at least three different types of polymers including a pH dependent gelling polymer, a pH independent gelling polymer and an enteric polymer, wherein said pH independent gelling polymer comprises at least one of a hydroxy propyl methyl cellulose, a hydroxy propyl ethyl cellulose, a hydroxy propyl cellulose, a hydroxy ethyl cellulose, a methyl cellulose, a xantham gums or a polyethylene oxide.

3. A tablet for sustained release of a drug comprising an effective amount of a drug to be released at a controlled rate and a sustained release formulation, said sustained release formulation comprising at least three different types of polymers including a pH dependent gelling polymer, a pH independent gelling polymer and an enteric polymer, wherein said enteric polymer comprises at least one of a polyacrylate material, a cellulose acetate phthalate, a cellulose phthalate hydroxy propyl methyl ether, a polyvinyl acetate phthalate, a hydroxy propyl methyl cellulose acetate succinate, a cellulose acetate trimellitate, or a shellac.

4. A tablet as set forth in claim 1, 2 or 3, wherein said drug comprises one or more of a water soluble, water sparingly soluble or water insoluble active material.

5. A tablet as set forth in claim 1, 2 or 3, wherein the content of said drug in said formulation ranges from about 0.5% to about 70% by weight thereof.

6. A tablet for sustained release of an active material comprising a sustained release formulation, said sustained release formulation comprising at least three different types of polymers including a pH dependent gelling polymer, a pH independent gelling polymer and an enteric polymer, wherein said pH dependent gelling polymer comprises at least one of an alginate, a carboxyvinyl polymer, or a salt of a carboxymethyl cellulose.

7. A formulation for sustained release of an active material, said sustained release formulation comprising at least three different types of polymers including a pH dependent gelling polymer, a pH independent gelling polymer and an enteric polymer, wherein said pH dependent gelling polymer comprises at least one of an alginate, a carboxyvinyl polymer, or a salt of a carboxymethyl cellulose.

8. A tablet for sustained release of an active material comprising a sustained release formulation, said sustained release formulation comprising at least three different types of polymers including a pH dependent gelling polymer, a pH independent gelling polymer and an enteric polymer, wherein said pH independent gelling polymer comprises at least one of a hydroxy propyl methyl cellulose, a hydroxy propyl ethyl cellulose, a hydroxy propyl cellulose, a hydroxy ethyl cellulose, a methyl cellulose, a xantham gum, or a polyethylene oxide.

9. A formulation for sustained release of an active material, said sustained release formulation comprising at least three different types of polymers including a pH dependent gelling polymer, a pH independent gelling polymer and an enteric polymer, wherein said pH independent gelling polymer comprises at least one of a hydroxy propyl methyl cellulose, a hydroxy propyl ethyl cellulose, a hydroxy propyl cellulose, a hydroxy ethyl cellulose, a methyl cellulose, a xantham gum, or a polyethylene oxide.

10. A tablet for sustained release of an active material comprising a sustained release formulation, said sustained release formulation comprising at least three different types of polymers including a pH dependent gelling polymer, a pH independent gelling polymer and an enteric polymer, wherein said enteric polymer comprises at least one of a polyacrylate material, a cellulose acetate phthalate, a cellulose phthalate hydroxy propyl methyl ether, a polyvinyl acetate phthalate, a hydroxy propyl methyl cellulose acetate succinate, a cellulose acetate trimellitate, or a shellac.

11. A formulation for sustained release of an active material, said sustained release formulation comprising at least three different types of polymers including a pH dependent gelling polymer, a pH independent gelling polymer and an enteric polymer, wherein said enteric polymer comprises at least one of a polyacrylate material, a cellulose acetate phthalate, a cellulose phthalate hydroxy propyl methyl ether, a polyvinyl acetate phthalate, a hydroxy propyl methyl cellulose acetate succinate, a cellulose acetate trimellitate, or a shellac.

12. A tablet as set forth in claim 1, wherein said pH independent gelling polymer comprises at least one of a hydroxy propyl methyl cellulose, a hydroxy propyl ethyl cellulose, a hydroxy propyl cellulose, a hydroxy ethyl cellulose, a methyl cellulose, a xantham gum, or a polyethylene oxide, and wherein said enteric polymer comprises at least one of a polyacrylate material, a cellulose acetate phthalate, a cellulose phthalate hydroxy propyl methyl ether, a polyvinyl acetate phthalate, a hydroxy propyl methyl cellulose acetate succinate, a cellulose acetate trimellitate, or a shellac.

13. A tablet as set forth in claim 6, wherein said pH independent gelling polymer comprises at least one of a hydroxy propyl methyl cellulose, a hydroxy propyl ethyl cellulose, a hydroxy propyl cellulose, a hydroxy ethyl cellulose, a methyl cellulose, a xantham gum, or a polyethylene oxide, and wherein said enteric polymer comprises at least one of a polyacrylate material, a cellulose acetate phthalate, a cellulose phthalate hydroxy propyl methyl ether, a polyvinyl acetate phthalate, a hydroxy propyl methyl cellulose acetate succinate, a cellulose acetate trimellitate, or a shellac.

14. A formulation as set forth in claim 7, wherein said pH independent gelling polymer comprises at least one of a hydroxy propyl methyl cellulose, a hydroxy propyl ethyl cellulose, a hydroxy propyl cellulose, a hydroxy ethyl cellulose, a methyl cellulose, a xantham gum, or a polyethylene oxide, and wherein said enteric polymer comprises at least one of a polyacrylate material, a cellulose acetate phthalate, a cellulose phthalate hydroxy propyl methyl ether, a polyvinyl acetate phthalate, a hydroxy propyl methyl cellulose acetate succinate, a cellulose acetate trimellitate, or a shellac.

15. The invention of claim 1, 6, 7, 12, 13, or 14, wherein said pH dependent gelling polymer comprises an alginate.

16. The invention of claim 1, 6, 7, 12, 13, or 14, wherein said pH dependent gelling polymer comprises a carboxyvinyl polymer.

17. The invention of claim 1, 6, 7, 12, 13, or 14, wherein said pH dependent gelling polymer comprises a salt of a carboxymethyl cellulose.

18. The invention of claim 2, 8, 9, 12, 13, or 14, wherein said pH independent gelling polymer comprises a hydroxy propyl methyl cellulose.

19. The invention of claim 2, 8, 9, 12, 13, or 14, wherein said pH independent gelling polymer comprises a hydroxy propyl ethyl cellulose.

20. The invention of claim 2, 8, 9, 12, 13, or 14, wherein said pH independent gelling polymer comprises a hydroxy propyl cellulose.

21. The invention of claim 2, 8, 9, 12, 13, or 14, wherein said pH independent gelling polymer comprises a hydroxy ethyl cellulose.

22. The invention of claim 2, 8, 9, 12, 13, or 14, wherein said pH independent gelling polymer comprises a methyl cellulose.

23. The invention of claim 2, 8, 9, 12, 13, or 14, wherein said pH independent gelling polymer comprises a xantham gum.

24. The invention of claim 2, 8, 9, 12, 13, or 14, wherein said pH independent gelling polymer comprises a polyethylene oxide.

25. The invention of claim 3, 10, 11, 12, 13, or 14, wherein said enteric polymer comprises a polyacrylate material.

26. The invention of claim 3, 10, 11, 12, 13, or 14, wherein said enteric polymer comprises a cellulose acetate phthalate.

27. The invention of claim 3, 10, 11, 12, 13, or 14, wherein said enteric polymer comprises a cellulose phthalate hydroxy propyl methyl ether.

28. The invention of claim 3, 10, 11, 12, 13, or 14, wherein said enteric polymer comprises a polyvinyl acetate phthalate.

29. The invention of claim 3, 10, 11, 12, 13, or 14, wherein said enteric polymer comprises a hydroxy propyl methyl cellulose acetate succinate.

30. The invention of claim 3, 10, 11, 12, 13, or 14, wherein said enteric polymer comprises a cellulose acetate trimellitate.

31. The invention of claim 3, 10, 11, 12, 13, or 14, wherein said enteric polymer comprises a shellac.

32. The invention of claim 25, wherein said polyacrylate material comprises a methacrylic acid polymer.

33. The invention of claim 1, 2, 3, 6, 7, 8, 9, 10, or 11, wherein said enteric polymer comprises a methacrylic acid copolymer.

34. The invention of claim 1, 2, 3, 6, 7, 8, 9, 10, or 11, wherein said pH dependent gelling polymer comprises a sodium alginate.

35. The invention of claim 1, 2, 3, 6, 7, 8, 9, 10, or 11, wherein said pH independent gelling polymer comprises a hydroxy propyl methyl cellulose.

36. The invention of claim 1, 2, 3, 6, 7, 8, 9, 10, or 11, wherein said pH independent gelling polymer comprises a hydroxy propyl ethyl cellulose.

37. The invention of claim 1, 2, 3, 6, 7, 8, 9, 10, or 11, wherein said pH independent gelling polymer comprises a polyethylene oxide.

38. The invention of claim 1, 2, 3, 6, 7, 8, 9, 10, or 11, wherein said enteric polymer comprises a cellulose acetate phthalate.

39. The invention of claim 1, 2, 3, 6, 7, 8, 9, 10, or 11, wherein said pH dependent gelling polymer comprises a sodium carboxy methyl cellulose.

40. The invention of claim 1, 6, or 7, wherein said enteric polymer comprises a methacrylic acid copolymer, said pH dependent gelling polymer comprises a sodium alginate, and said pH independent gelling polymer comprises a hydroxy propyl methyl cellulose.

41. The invention of claim 1, 6, or 7, wherein said enteric polymer comprises a methacrylic acid copolymer, said pH dependent gelling polymer comprises a sodium alginate, and said pH independent gelling polymer comprises a polyethylene oxide.

42. The invention of claim 1, 6, or 7, wherein said enteric polymer comprises a methacrylic acid copolymer, said pH dependent gelling polymer comprises a sodium alginate, and said pH independent gelling polymer comprises a hydroxy propyl ethyl cellulose.

43. The invention of claim 1, 6, or 7, wherein said enteric polymer comprises a cellulose acetate phthalate, said pH dependent gelling polymer comprises a sodium carboxy methyl cellulose, and said pH independent gelling polymer comprises a hydroxy propyl methyl cellulose.

44. The invention of claim 1, 2, 3, 6, 7, 8, 9, 10, 11, 12, 13, or 14, wherein the total content of said gelling and enteric polymers in said formulation ranges from about 8% to about 65% by weight thereof.

45. The invention of claim 1, 2, 3, 6, 7, 8, 9, 10, 11, 12, 13, or 14, wherein the content of said pH dependent gelling polymer in said formulation ranges from about 2% to about 60% by weight thereof.

46. The invention of claim 1, 2, 3, 6, 7, 8, 9, 10, 11, 12, 13, or 14, wherein the content of said pH independent gelling polymer in said formulation ranges from about 2% to about 55% by weight thereof.

47. The invention of claim 1, 2, 3, 6, 7, 8, 9, 10, 11, 12, 13, or 14, wherein the content of said enteric polymer in said formulation ranges from about 1% to about 55% by weight thereof.

* * * * *